United States Patent [19]

Calzi

[11] Patent Number: 4,490,235
[45] Date of Patent: Dec. 25, 1984

[54] ELECTROCHEMICAL CELL PROVIDED WITH SELECTIVE ELECTRODES AND AT LEAST ONE CHEMICAL REACTOR, FOR INDIRECT MEASUREMENT OF CLINICAL-CHEMICAL PARAMETERS

[75] Inventor: Claudio Calzi, 8 Via Popoli Uniti, Milan, Italy, 20125

[73] Assignee: Claudio Calzi, Milan, Italy

[21] Appl. No.: 396,090

[22] Filed: Jul. 7, 1982

[30] Foreign Application Priority Data

Jul. 13, 1981 [IT] Italy .................... 22887 A/81

[51] Int. Cl.³ .................................... G01N 27/46
[52] U.S. Cl. .......................... 204/409; 204/1 T; 204/411; 204/416; 204/433
[58] Field of Search .......... 204/1 T, 400, 403, 409, 204/416, 418–420, 411, 433

[56] References Cited

U.S. PATENT DOCUMENTS

| 3,151,052 | 9/1964 | Arthur et al. | 204/409 |
|---|---|---|---|
| 3,306,837 | 2/1967 | Riseman et al. | 204/420 |
| 3,408,269 | 10/1968 | Hersch | 204/1 K |
| 3,479,255 | 11/1969 | Arthur | 204/1 T |
| 3,620,931 | 11/1971 | Reichner | 204/426 |
| 3,707,455 | 12/1972 | Derr et al. | 204/403 |
| 3,846,257 | 11/1974 | Riseman et al. | 204/419 |
| 3,865,708 | 2/1975 | Light et al. | 204/419 |
| 3,896,008 | 7/1975 | Keyes | 204/403 |

Primary Examiner—T. Tung
Attorney, Agent, or Firm—Wenderoth, Lind & Ponack

[57] ABSTRACT

An electrochemical cell is provided with plural identical selective electrodes and at least one chemical reactor for the indirect measurement of clinical-chemical parameters. The electrodes are ion-selective for the same ionic species or gas-selective for the same gaseous species. One of the two electrodes can be used as a measuring electrode and the other as a reference electrode. In the case of gas-selective electrodes, the reference electrode can be selective for a different ionic species. A third electrode with just electrical conducting properties can be provided. The chemical reactor can utilize immobilized enzymes, or immobilized substrates, or ion exchange resins, and is preferably connected to the measuring electrode only. Two fluidic paths may be provided in the electrochemical cell, as well as one input and two outputs, or two inputs and just one output in sequence. More sophisticated types of apparatus based on the same principles, can incorporate two or more different chemical reactors, or else reactors which can be connected to both the measuring and the reference electrodes, the respective functions of which can be exchanged, or the apparatus can employ a plurality of elementary electrochemical cells.

10 Claims, 5 Drawing Figures

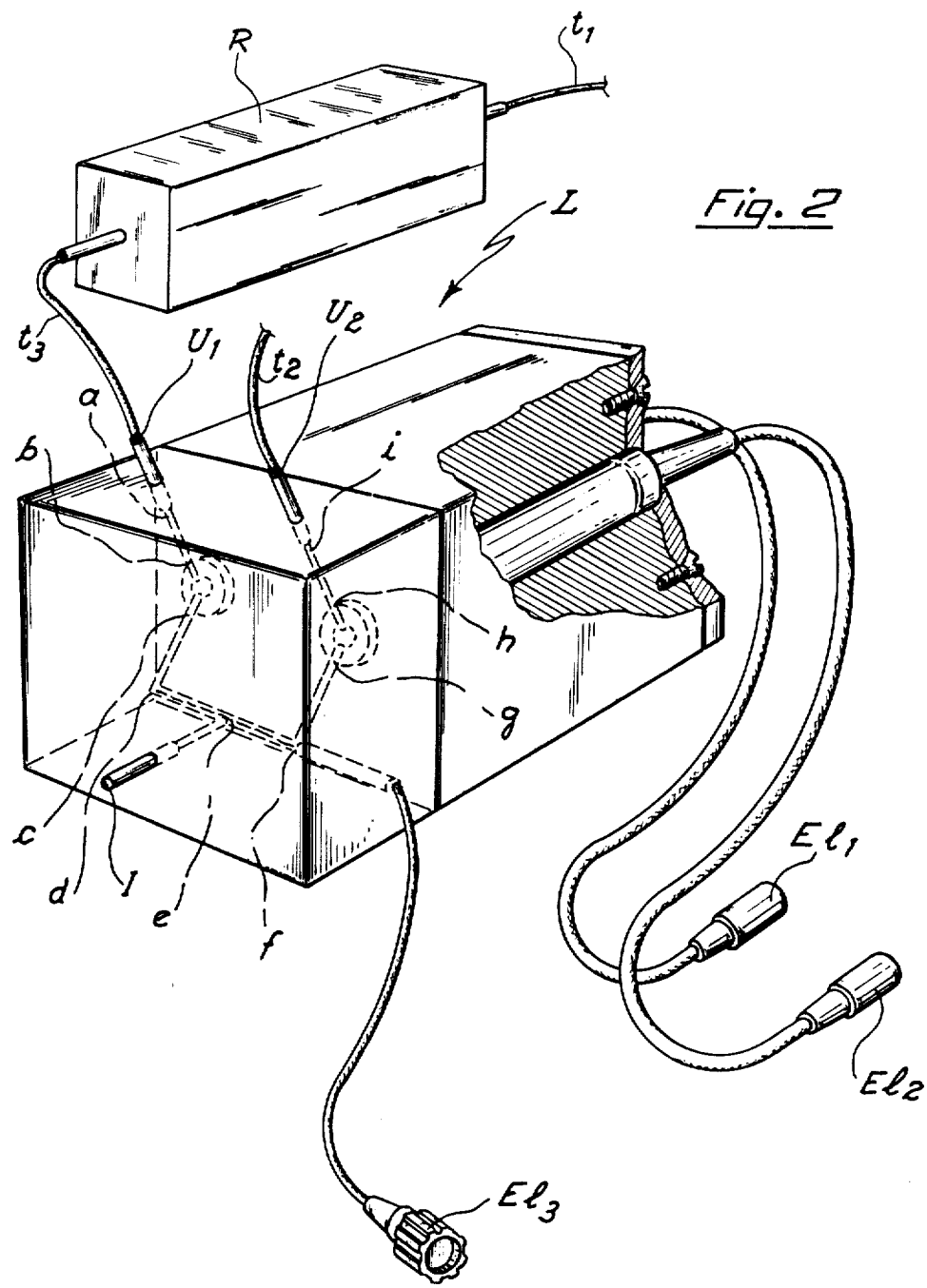

ELECTROCHEMICAL CELL PROVIDED WITH SELECTIVE ELECTRODES AND AT LEAST ONE CHEMICAL REACTOR, FOR INDIRECT MEASUREMENT OF CLINICAL-CHEMICAL PARAMETERS

BACKGROUND OF THE INVENTION

Various apparatus for measuring substances, mainly used in clinical chemistry are already well known (See above all those of Yellow Spring Instrument Co. for measuring glucose and galactose, and those of Owens-Illinois (Kimble Division) for measuring urea). These types of apparatus use enzymatic electrodes, that is, electrochemical sensors on whose sensitive external membrane are deposited reactive substances such as enzymes.

By means of such apparatus, it is possible to measure indirectly other substances capable of reacting with the enzyme, forming a reaction product which can be detected by the electrode employed. By way of example, it is well known in documentation how it is possible to determine the concentration of glucose in the presence of glucos-oxidase enzyme, by measuring the oxygen used up in the reaction:

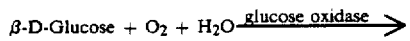

$\beta$-D-Glucose + $O_2$ + $H_2O$ $\xrightarrow{\text{glucose oxidase}}$ $H_2O_2$ + D-gluconic acid In this case, a gas electrode, known as the Clark electrode, for measuring $pO_2$, is used.

Another well known reaction is that for determining urea in the presence of urease enzymes, by measuring the ammonia $NH_3$ or the $NH_4^+$ ion. Particularly, among the patents of the prior art the following are also to be mentioned. DS-Pat. No. 1,956,211 (Beckmann) uses electrochemical sensors, well known, suitable for direct differential measurement of $SO_2$. The present invention provides instead an analyzer that measures a parameter which is indirectly correlated or can be correlated to another parameter. Therefore the Beckmann apparatus is not able to solve the problems recognized by the inventor, in that it offers the possibility of measuring only one parameter.

Moreover, the Beckman patent provides only one measurement phase, rather than a series of phases consisting of filling, measurement, advancement, reaction, return and final measuring of a fluid. A succession of phases like this assures much more significant and varied results. The subject of the U.S. Pat. No. 3,909,204 (J. D. Allen) is an apparatus for measuring $N_2O$ and $CO_2$ through a galvanic cell. Generally speaking, measurements made with these types of apparatus are not altogether reliable, as the final element ($pO_2$, $pNH_4^+$ etc.) to be determined is also present in a sample under investigation in an unknown quantity, together with interfering substances for the sensor employed.

SUMMARY OF THE INVENTION

In order to remedy this defect, the present inventor has thought of using an electrochemical cell which was the subject of his Italian patent application No. 22647 A/81 filed 30.6.81 and which is provided with selective electrodes, preferably two in number and identical with respect to each other, of which one is used as a measuring electrode and the other as a reference electrode.

This cell is also provided with—and in this provision lies the main feature of the present invention—at least one chemical reactor, and contains two internal fluidic paths in which part of the substance to be measured can come into contact with the measuring electrode and the reactor, and the other part of the substance can, respectively, come into contact with the reference electrode only. Hence the cell is suitable for indirect measurement of the clinical-chemical parameters of a substance. Such cell is also characterized in that the selective electrodes can be ion-selective or gas-selective, and, in the first case be preferably ion-selective for the same ionic species, and in the second case be preferably gas-selective for the same gaseous species.

As variants, cells can be provided with two ion-selective electrodes for different species, with just one gas-selective measuring electrode without a reference electrode, and with a third electrode with just electrical conducting properties. Thirdly, the cell in accordance with the invention is characterized in that a chemical reactor is provided which can use immobilized enzymes or immobilized substrates, or, if required, ion exchange resins. Fourthly, the cell in accordance with the invention is characterized in that two or more different chemical reactors may be provided, in which case the cell can carry out indirect sequential measurements of various clinical-chemical parameters of the same substance. Fifthly, the cell in accordance with the invention is characterized in that the chemical reactor or reactors can be connected both to the measuring electrode and to the reference electrode, hence these electrodes can have their respective functions interchanged at a later date.

The cell of the present invention can be used in a method of measurement consisting in using at least one of the above described electro-chemical cells and is based on two consecutive measurements above all on the sample under investigation when—with the cell completely filled by it—it comes into contact with the measuring electrode, the chemical reactor or reactors, and the reference electrode if this is also present, and, afterwards, on just those parts of the sample which have reacted in the reactor, or in the reactors, when they return in contact with the measuring electrode.

It is clear that with such method of measurement, it is possible on the one hand to eliminate the so-called background effect as measurements can be made independently of the value of the species under investigation contained in the sample, and on the other hand to eliminate virtually all the interfering substances, as regards the sensors, present in the sample and unreacted in the reactor. Hence very appreciable progress can be achieved with such a method.

Since this method, as can be easily deduced by persons skilled in the art, can be applied to a plurality of chemical for the determination of, for example, glucose, urea, creatinine, lactic acid, cholesterol, triglycerides, amino acids etc., and certain enzymatic activities such as cholinestrase, etc. concentrations of ionic species such as $Li^+$, $Na^+$, $K^+$, $Ca^+$, etc. shows just how highly important it is.

BRIEF DESCRIPTION OF THE DRAWING

The novelty of the electrochemical cell in accordance with the invention will appear even clearer from the following description, with reference to the accompanying drawings given only as a rough guide to the principles of the invention.

FIG. 2 is a perspective view of such cell with a part removed for clarity; and

DETAILED DESCRIPTION OF THE INVENTION

Figure 1:
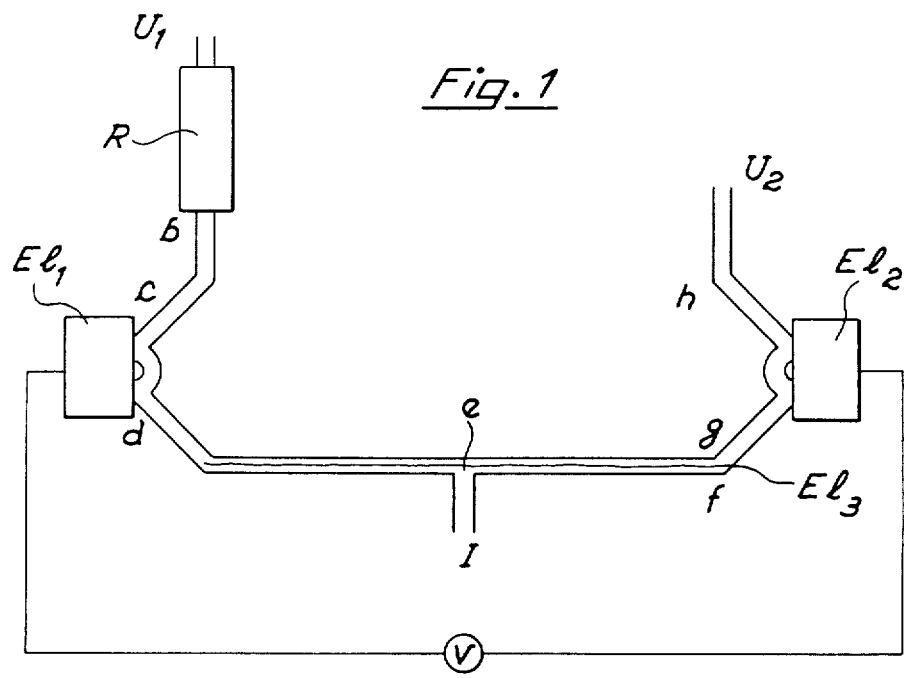
FIG. 1 is a schematic view of a particularly simple preferred embodiment of the electrochemical cell of the invention.

As can be seen in the drawings (FIGS. 1 and 2), the electrochemical cell in question is essentially provided with a measuring electrode $El_1$, a reference electrode $El_2$, and, if required (as illustrated schematically in FIGS. 1, 4 and 5) a third electrode $El_3$ with just electrical conductivity properties, as well as, characteristically, a chemical reactor R. Inside the electrochemical cell of FIG. 1, there are two separate fluidic circuits e,d,c,b, and e,f,g,h, both commencing from the same input I but having two separate outputs $U_1$, $U_2$, with one circuit being connected to measuring electrode $El_1$ and reactor R, and the other to reference electrode $El_2$, and both to a third electrode $El_3$ when required. The measurements—performed with the aid of voltmeter V—are made by comparison on the two different parts of the sample which have reacted or not in the zone of the two measuring and reference electrodes $El_1$ and $El_2$, both in the forward and return directions of the two fluidic circuits with respect to opening I which, in this case, not only functions as an input but also as an output. Obviously the apparatus containing the cell is designed to include a device whereby the two parts of the sample to be measured follow not just a forward path but one which goes back and forth.

The reactions and measurements which can be performed with the aid of the electrochemical cell in accordance with the above invention (see FIG. 1 or 2) and with the just described method are manifold. A particularly significant example of these reactions and measurements, is now given merely as guideline of the principles of the invention. Suppose the glucose content of a sample is to be determined by means of the reactions

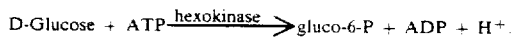

D-Glucose + ATP $\xrightarrow{\text{hexokinase}}$ gluco-6-P + ADP + $H^+$

In this case, the $H^+$ proportional to the glucose concentration is to be measured.

Suppose therefore $El_1$ and $El_2$ are both ion-selective electrodes for pH, $El_1$ being the measuring electrode and $El_2$ the reference electrode, while the chemical reactor R contains an immobilized hexokinase enzyme. The biological glucose-containing sample is diluted with a buffer solution where the pH value is approximate merely of an order to favour the reaction. Hence the pH of the sample-buffer solution is not exactly known. Now suppose the electrochemical cell C is completely filled with the sample and buffer solution so that the mixture affects the sections between input/output I, output/input $U_1$, output/input $U_2$. Both the electrodes $El_1$, $El_2$, which are identical, each one consisting of an electrochemical half-cell, will generate an equal electromotive force with respect to the solution added to the cell. Hence when potential V is measured in a differential manner, it will be found to be zero. Any practical deviations from zero can be corrected to zero by adjusting the measuring apparatus.

The third electrode $El_3$ is only necessary for operation of the electronic measuring apparatus used for reading the potential V of the liquid substance and therefore it does not take part in the actual measurement of the clinical-chemical parameters of the liquid substance. It houses the electric current (in the order of a few tenths of a femtoampere) flowing in the electrodes $El_1$ and $El_2$. Assuming this condition with V equal to zero, if the portion of solution contained in reactor R of FIG. 2 between points a and b of the cell is made to flow in the direction of input/output I, so that the solution previously between point b and e is expelled from the cell, and the solution previously contained in reactor R now affects points c, d, e, and therefore electrode $El_1$, and the situation regarding electrode $El_2$ is left unaltered, a potential V' will be measured which will be proportional to the $H^+$ of the reaction taken place in reactor R. This V' will assume a value proportional to the difference in ionic activity of the $H^+$ ion between the original solution and the reacted solution. Hence potential V' will be proportional to the concentration of glucose in the original sample.

The magnitude of V' is therefore an indication of the increase in the $H^+$ ion due to the reaction of the glucose in the reactor R. This V' can express a kinetic measurement of the reaction or a limiting measurement (that is, one taken place completely or in part). The standardization of the cell can be performed by conventional methods. First of all, a sample with zero glucose content is introduced in order to zero the measuring system. Next a sample with a known glucose content is introduced and the corresponding V' measured.

Strictly speaking, the system consisting of the two electrodes $El_1$ and $El_2$ measures not only the difference in ionic activity between the two solutions, but also the liquid junction potential between the solutions. However this can be easily taken into account during calibration. This problem does not exist at all in the case of gas electrodes $El_1$ and $El_2$. Furthermore, in the case of the gas electrodes, the cell can be simplified in many applications through the elimination of the reference electrode.

Figure 4:
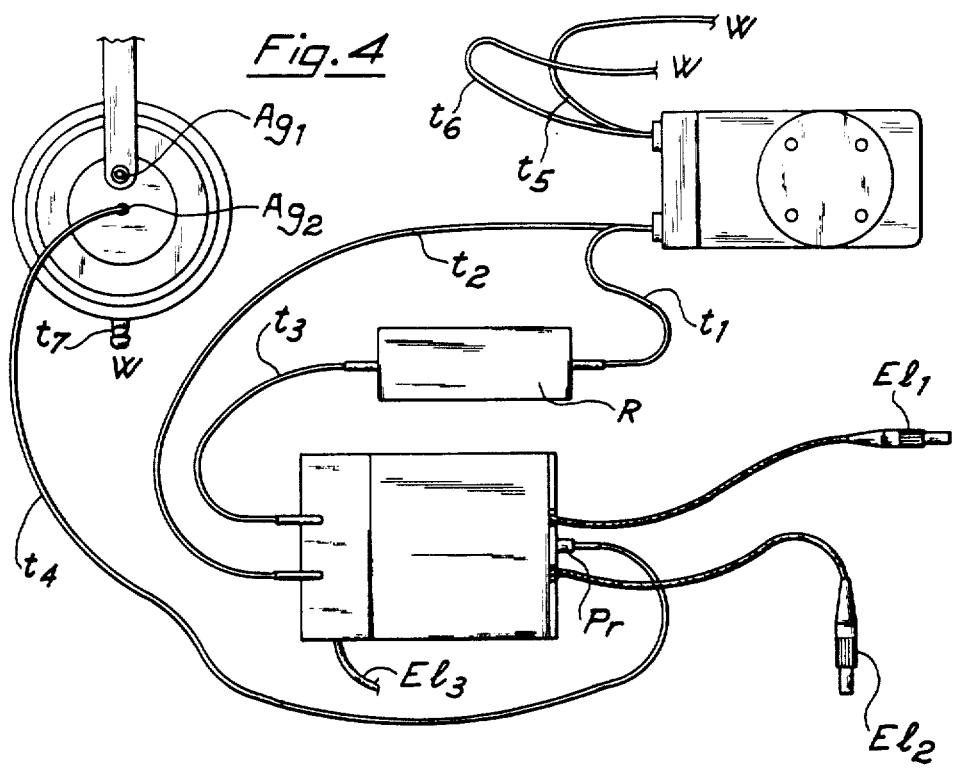
Figure 5:
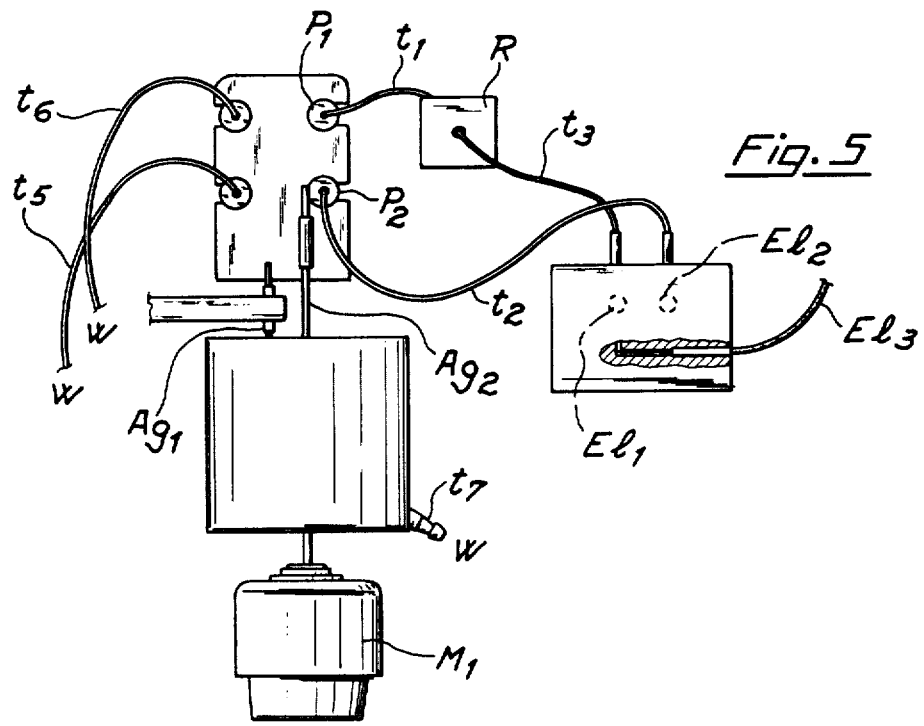

Referring to FIGS. 1 and 2, the portion of the cell comprising measuring electrode $El_1$ and reactor R is used. First of all, the solution under investigation is added through input/output I until the cell and reactor R are completely full. The partial pressure of the gas present in the sample is measured first by means of electrode $El_1$. Next, the content of reactor R, section a, and section b is transferred so that it affects the measuring chamber with electrode $El_1$ at section c, d. The new partial pressure is then measured. The difference between the first and second measurement will obviously furnish a value proportional to the species under measurement. But for a clearer understanding of the method of measurement employing the cell of this invention, it is preferable to consider FIGS. 3,4,5 showing a measuring apparatus taken as a whole, of which the electrochemical cell is the essential feature.

As can be seen in these figures, the apparatus besides comprising the electrochemical cell C, also comprises a vessel Co of truncated cone shape rotated by means of a motor $M_1$ and into which the sample under investigation is added through a first capillary needle $Ag_1$.

Also provided are two peristaltic pumps $P_1$ and $P_2$ driven by motor $M_2$ which has two directions of rotation. The $P_1$ pump is connected by means of tube $t_1$ to chemical reactor R which, for fluidic purposes, corresponds to a portion of a tube and which is, in turn, connected by another tube $t_3$ to the part of the chamber of cell C provided with measuring electrode $El_1$. Pump $P_2$ is, instead, connected by means of tube $t_2$ to the part or chamber of cell C provided with reference electrode $El_2$. The two parts or chambers of cell C converge at point e in FIGS. 1 and 2 and they run into metal tube Pr in FIGS. 3 and 4, connected, in turn, to a second capillary needle Ag2 capable of aspirating through a tube $t_4$, the sample substance from the vessel Co. The remaining connections of pumps $P_1$ and $P_2$ are (see FIGS. 4 and 5) to drain W through tubes $t_5$ and $t_6$. Operation of the apparatus is already clear from the foregoing description.

Figure 3:
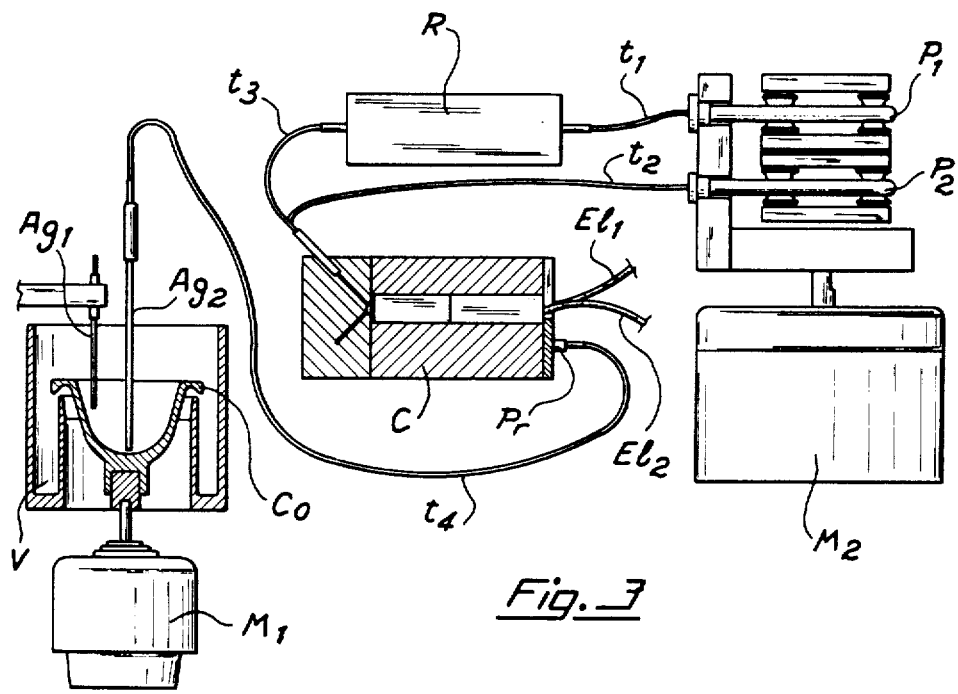
FIGS. 3, 4, 5 are a front view, a top view and a side view, respectively, of an apparatus whose essential characterizing feature is an electrochemical cell in accordance with the invention, and which is therefore suitable for indirect measurements of clinical-chemical parameters of a substance.

By actuating motor $M_2$ in FIG. 3, e.g. in the clockwise direction, the sample is aspirated from vessel Co so as to completely fill, tube $t_4$, metal tube Pr, the chambers of cell C provided with electrodes $El_1$ and $El_2$, respectively, tube $t_3$, reactor R, tube $t_1$ and tube $t_2$, as well as the tubes of pumps $P_1$ and $P_2$. After this, motor $M_2$ is stopped.

The first measurement of the potential difference between electrodes $El_1$ and $El_2$ is performed under these conditions, using an electronic voltmeter and instrument compensation is made, if required. After carrying out this first measurement, motor $M_2$ is again actuated in the opposite direction to the preceding one, that is counter-clockwise, for a period sufficient to allow the reacted sample contained in reactor R to travel to the chamber of electrochemical cell C provided with measuring electrode $El_1$. The sample contained in tube $t_2$ is also moved and travels to the other chamber of electrochemical cell C provided with reference electrode $El_2$. After this, motor $M_2$ is stopped.

We now have a condition in which the reacted sample is present in the first chamber with measuring electrode $El_1$, while the original sample is present in the measuring chamber with reference electrode $El_2$. Under this condition, a second measurement is again carried out of the potential difference between electrode $El_1$ and $El_2$, which will be proportional to the species under measurement. Owing to the counter-clockwise direction of operation of pumps $P_1$ and $P_2$, a mixture consisting of the original sample and the sample which has reacted in reactor R is pumped back to vessel Co. This mixture plus any residue of the sample originally present in vessel Co is no longer of practical use.

By actuating motor $M_1$ in FIG. 3 for a certain period, the residual liquid in vessel Co will, owing to the effect of centrifugal force, be expelled from, chamber V and will be conveyed, via tube $t_7$, to drain W. At this point, the apparatus is now ready to carry out a new analysis. For a person skilled in the art, as stated previously, it will be clear that both the electrochemical cell and the apparatus of which it is an essential part can undergo numerous variations without departing from the scope, hence the applications are vast. The exact limitations of the invention are set forth in the appended claims.

I claim:

1. An electrochemical cell for indirect measurement of clinical-chemical parameters of a liquid substance, comprising:
    a chemical reactor;
    a first selective electrode means for measuring a clinical-chemical parameter of the liquid substance before the flow of the liquid substance enters into the chemical reactor and again after the liquid substance reverses its flow out of the chemical reactor;
    a second selective electrode means for being a reference electrode;
    two distinct internal fluidic path means for allowing passage of the liquid substance so that one part of the liquid substance passes through a first path into contact with the measuring electrode means and the chemical reactor and then reverses its flow back out of contact with the chemical reactor and the measuring electrode means, and another part of the liquid substance passes through a second path into contact with just the reference electrode means;
    a single tube means for inputting the liquid substance to be measured into the two fluidic path means and for outputting the liquid substance from the two fluidic path means after measurement, said single tube means having two outputs connected to the two fluidic path means; and
    motor means for reversing flow of the liquid substance in the chemical reactor;
    whereby two consecutive measurements are carried out on the liquid substance, first, when the liquid substance initially comes into contact with the measuring electrode means, the chemical reactor, and the reference electrode means, and, second, on just part of the liquid substance which has reacted in the chemical reactor when that part of the liquid substance has reversed its flow back into contact with the measuring electrode means, so that the clinical-chemical parameter of the liquid substance can be measured.

2. An electrochemical cell as claimed in claim 1, wherein said electrode means are ion-selective for the same ionic species.

3. An electrochemical cell as claimed in claim 1, wherein said electrode means are gas-selective for the same gaseous species.

4. An electrochemical cell as claimed in claim 1, wherein said reference electrode means is ion-selective for a species differing from that of the liquid substance to be measured.

5. An electrochemical cell as claimed in claim 1, wherein said measuring electrode means is gas-selective.

6. An electrochemical cell as claimed in claim 1, wherein said chemical reactor uses one of immobilized enzymes and immobilized substrates.

7. An electrochemical cell as claimed in claim 1, wherein said chemical reactor uses ion exchange resins.

8. An electrochemical cell as claimed in claim 1, further comprising:
    a third electrode means, provided with just electrical conducting properties, for measuring electrical potential of the liquid substance.

9. An electrochemical cell as claimed in claim 1, further comprising:
    at least a second chemical reactor,
    whereby said electrochemical cell is used for sequential indirect measurement of other clinical-chemical parameters of the liquid substance.

10. An electrochemical cell as claimed in claim 9, wherein said chemical reactors are connectable both to said measuring electrode means and to said reference electrode means, whereby the respective functions of said electrode means are exchangeable.

* * * * *